United States Patent
Autrey et al.

(10) Patent No.: US 6,244,101 B1
(45) Date of Patent: Jun. 12, 2001

(54) PHOTOACOUSTIC METHOD FOR MEASURING CONCENTRATION OF CHEMICAL SPECIES

(75) Inventors: S. Thomas Autrey, West Richland; Gerald J. Posakony, Richland; James E. Amonette, Richland; Nancy S. Foster-Mills, Richland, all of WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/322,910

(22) Filed: Jun. 1, 1999

(51) Int. Cl.[7] .................................................. G01N 21/17
(52) U.S. Cl. ..................... 73/61.45; 73/24.02; 73/61.49; 356/432
(58) Field of Search ......................... 73/24.02, 24.01, 73/61.45, 61.49, 61.75, 61.79; 356/432, 437; 250/343, 351, 339.12, 339.13, 338.5

(56) References Cited

U.S. PATENT DOCUMENTS

| | | | |
|---|---|---|---|
| 4,051,371 | 9/1977 | Dewey, Jr. et al. | 250/339.13 |
| 4,303,343 | * 12/1981 | Patel et al. | 356/432 |
| 5,616,826 | * 4/1997 | Pellaux et al. | 73/24.02 |
| 5,933,245 | * 8/1999 | Wood et al. | 356/432 |
| 6,160,255 | * 12/2000 | Sausa | 250/338.5 |

OTHER PUBLICATIONS

D Lynch et al., "A Pulsed Photoacoustic Microcalorimeter for the Detection of Upper Excited–State Processes and Intersystem Crossing Yields", *Applied Spectroscopy*, vol. 43, No. 5, 1989, pp. 826–833.

* cited by examiner

Primary Examiner—John E. Chapman
(74) Attorney, Agent, or Firm—Paul W. Zimmerman

(57) ABSTRACT

The present invention is a transducer for photoacoustic detection having at least two piezoelectric elements wherein at least a first piezoelectric element has a first frequency and at least a second piezoelectric element has a second frequency. The improvement according to the present invention is that at least two piezoelectric elements are longitudinal elements for longitudinal waves; and the first frequency is different from said second frequency. In other words, the invention is a multi-frequency longitudinal transducer for photoacoustic detection.

6 Claims, 4 Drawing Sheets

PHOTOACOUSTIC METHOD FOR MEASURING CONCENTRATION OF CHEMICAL SPECIES

This invention was made with Government support under Contract DE-AC0676RLO1830 awarded by the U.S. Department of Energy. The Government has certain rights in the invention.

FIELD OF THE INVENTION

The present invention is a multi-frequency acoustic transducer.

BACKGROUND OF THE INVENTION

Photoacoustic detection uses piezoelectric transducers to measure pressure waves from the radiationless decay of a laser excited state, generated by pulsed irradiation. The conversion of energy to heat generates a pressure wave that can be detected with a piezoelectric transducer. Presently, photoacoustic detection is a very sensitive technique but it is not very selective.

Traditionally, two types of dual element transducers are commercially available. First, a dual element longitudinal transducer in a single housing wherein both elements are matched to have the same frequency, for example 1 MHz and 1 MHz, or 5 MHz and 5 MHz, have been used for thickness gauging and/or flaw characterization. One element is used for transmitting a signal and the second is used for receiving the returned signal. The two matched elements are angled toward one another to create a crossed beam sound path to yield better near surface resolution. In making these dual element longitudinal transducers, the frequencies are carefully matched in order to assure an optimum transmitter/receiver beam overlap. The second type of commercially available photoacoustic transducer is a dual element longitudinal/shear wave transducer in a single housing. This is used to make both longitudinal and shear wave measurements with a single transducer. For example a longitudinal element may have a frequency of 1 MHz and the shear element may have a frequency of 2.5 MHz. Each element is specific for either shear waves or longitudinal waves. This second type is used for specific applications where the transducer may be fixed in order to obtain both the longitudinal and shear wave signals. Couplants used for acoustic scanning do not transmit shear wave signals.

In both types of transducers, the amplitude of the observed photoacoustic signal provides the sensitivity, i.e. measurement of the quantity of absorbing species. However, the selectivity, i.e. identifying the absorbing species in a mixture may be possible by seeking one or more wavelengths that is/are not absorbed by certain species of the mixture. Because of overlap of absorption spectra, this technique is limited to mixtures of species with limited absorption spectra overlap.

Thus, there is a need in the art for a photoacoustic transducer that provides greater selectivity without relying upon limited absorption spectra overlap.

SUMMARY OF THE INVENTION

The present invention is a transducer for photoacoustic detection having at least two piezoelectric elements wherein at least a first piezoelectric element has a first frequency and at least a second piezoelectric element has a second frequency. The improvement according to the present invention is that at least two piezoelectric elements are longitudinal elements for detecting pressure waves; and the first frequency is different from said second frequency. The at least two piezoelectric elements are used as receivers only. In other words, the invention is a multi-frequency longitudinal transducer for photoacoustic detection.

It is an object of the present invention to provide a transducer for photoacoustic detection that is a multi-frequency longitudinal wave transducer.

It is another object of the present invention to provide a method of identifying and measuring chemical species in a mixture.

An important advantage of the present invention is increased selectivity with no reduction in sensitivity.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

BRIEF DESCRIPTION OF THE DRAWINGS

FIG. 1b is a cross section orthogonal to FIG. 1a.

DESCRIPTION OF THE PREFERRED EMBODIMENT(S)

Figure 1A:
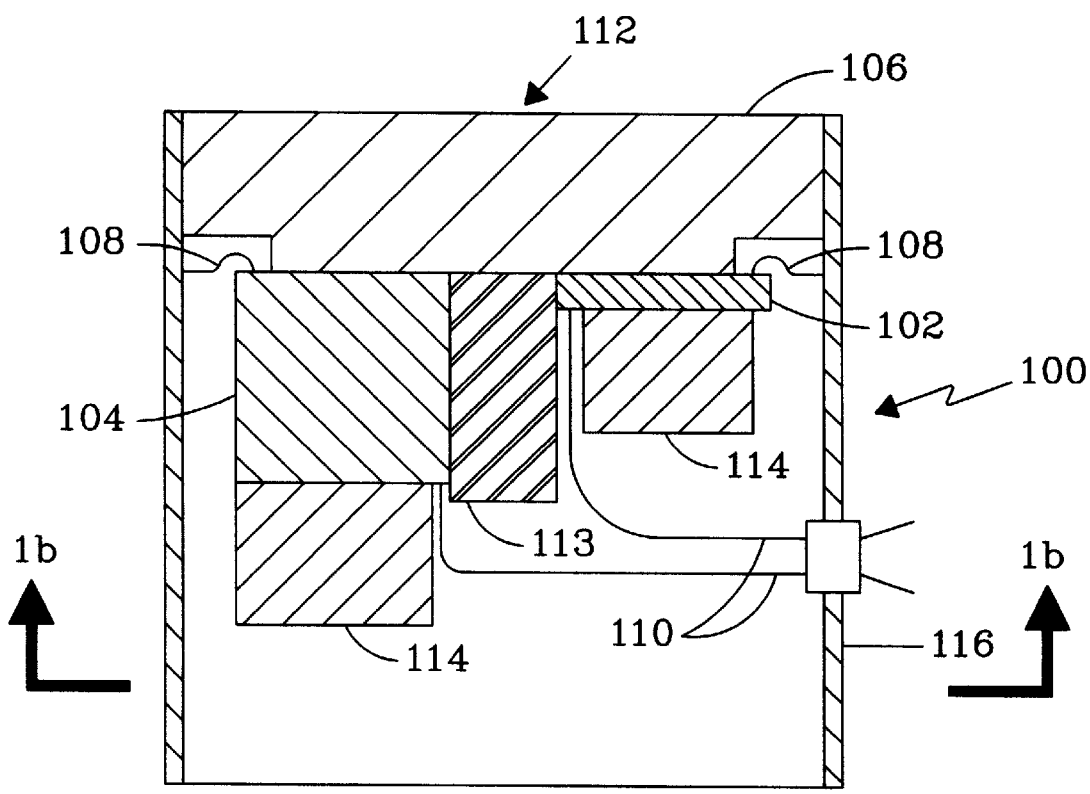
FIG. 1a is a cross section of a transducer according the present invention.

The present invention (FIG. 1a, FIG. 1b) is a transducer 100 for photoacoustic detection having at least two piezoelectric elements 102, 104. At least a first piezoelectric element 102 has a first frequency and at least a second piezoelectric element 104 has a second frequency. According to the present invention, the improvement is that at least two piezoelectric elements 102, 104 are longitudinal elements for longitudinal waves; and the first frequency is different from the second frequency. The present invention may be considered multi-frequency or multi-band for longitudinal waves.

In a preferred embodiment, at least two piezoelectric elements 102, 104 are mounted on a wear plate 106 and electrically connected to ground 108 and to load 110 as a subassembly 112. A barrier 113 is placed between the at least two piezoelectric elements 102, 104 to prevent crosstalk. A backing material 114 is optional. The subassembly 112 is preferably placed in a housing 116. The piezoelectric elements 102, 104 may be placed independently on the wear plate 106 as shown in FIG.'s 1a, 1b, or may be stacked as in FIG. 1c. When stacked, it is preferred to place an acoustic coupler 118 between the piezoelectric elements 102, 104. The wear plate 106 and the acoustic coupler 118 are preferably flat.

Figure 2:
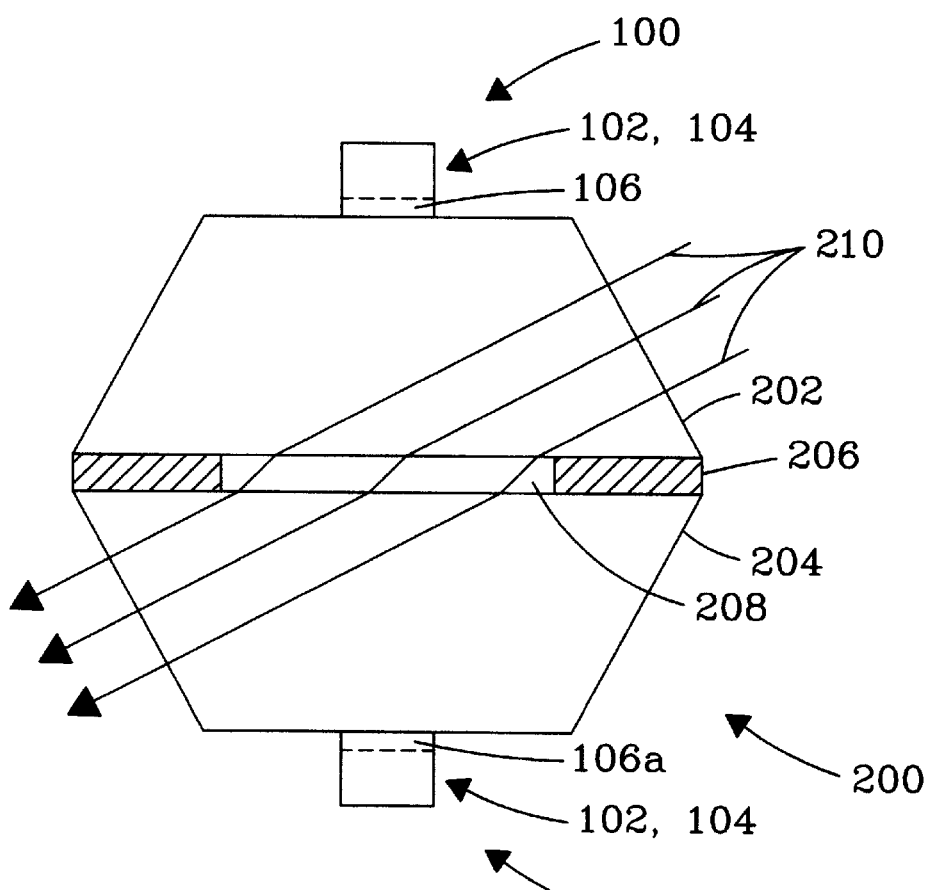
FIG. 2 is a cross section of a layered prism cell.

In another embodiment, especially when used in combination with a layered prism cell (FIG. 2), The at least two piezoelectric elements 102, 104 may be on separate wear plates 106, 106a or on the same wear plate 106. The layered prism cell 200 has a first body 202 and a second body 204 with a spacer 206 defining the sample chamber 208. Electromagnetic energy 210 generates a photoacoustic signal within the sample chamber 208.

In any embodiment, the use of the at least two piezoelectric elements 102, 104 may be for redundancy for data confirmation, or preferably for determining species in a mixture.

The piezoelectric elements 102, 104 may be any piezoelectric material, for example ceramic, polymer and combinations thereof. It is preferred to use a ceramic material to obtain sufficient voltage with a small sized piezoelectric element. Preferred is Nova 3B, available from KERAMOS, Indianapolis, Ind., the piezoelectric elements coated with silver electrodes.

The wear plate 106 may be any material, but is preferably a material of low damping. Ceramic, metal, glass, plastic, epoxy and combinations thereof are examples of wear plate material. Certain polymers may be used, but most polymers would have too much damping. The thickness of the wear plate may be greater than ¼ wavelength because the transducer 100 is used in a receive mode only, and the thickness should not be equal to ½ wavelength to avoid cancelled signal. Also, in the receive mode, the thickness to diameter ratio is not critical. If the wear plate 106 is non-metallic, it may be coated with a metal to provide a ground connection. It is preferred that the wear plate 106 be sufficiently thin to avoid the downshifting of the frequency of the received signal.

The barrier 113 may be any material, but is preferably a material that is acoustically absorptive for the wavelengths of interest. Materials include but are not limited to rubber, cork, foam and combinations thereof.

Confirmation of data involves comparing the transducer response for at least two frequencies. When the parameters describing the response (phi and tau) match at both frequencies, the data are confirmed.

The present invention relies upon the amplitude of the observed photoacoustic signal for information on the quantity of absorbing species (sensitivity), and the waveshape of the observed photoacoustic signal for information on the identity of the absorbing species (selectivity). Although it is possible to use two or more excitation wavelengths, it is preferred to use fewer rather than greater to simplify the apparatus and subsequent analysis. A most preferred embodiment has a single excitation wavelength of radiation energy to generate the time dependent photoacoustic signal. The time dependent photoacoustic signal is analyzed at more than one frequency thereby enhancing selectivity with no sacrifice in sensitivity. Moreover, it may be possible to omit a comparative standard by fitting data from two or more frequencies.

Photoacoustic selectivity is achieved by analyzing the response of the various frequency transducers to the time-dependent release of heat from the electronic and/or vibrational excited state species. For example substituted hydrocarbons, chlorobenzene and phenol generally have excited state lifetimes significantly longer than the corresponding parent hydrocarbons, i.e., benzene. The response of a 1 MHz and a 5 MHz transducer will have a characteristic shape defined by the concentration and excited state lifetime of the species absorbing the pulsed energy. In a preferred embodiment, the excitation is provided by a pulsed energy source of electromagnetic radiation (laser) having a wavelength including but not limited to x-ray, ultraviolet, visible, near infrared, infrared and combinations thereof.

A simple scheme involving the competitive absorption of light by two species A and B (equation 1 and 2) is a useful model to illustrate the time dependent response, M(t) (equation 3), provided by an ultrasonic transducer.

$$A^* \rightarrow A + \text{heat} \quad (1)$$

$$B^* \rightarrow B + \text{heat} \quad (2)$$

$$M(t) = \{H_A(t) + H_B(t)\} * S(t) \quad (3)$$

M(t) is described by a convolution (*) of the sum of heat released from species A, $H_A(t)$, and from species B, $H_B(t)$, with the transducer response, S(t). The transducer response, S(t), (equation 4), is a dampened sine wave, where $v$ is the resonant frequency, i.e., 1 or 5 MHz, $\tau_o$ is the dampening constant of the transducer and K is an instrument constant.

$$S(t) \sim K[\exp(-t/\tau_o)\sin(vt)] \quad (4)$$

The time-dependent release of heat, $H_i(t)$, from species i is defined by the quantity of heat released, $\phi_i$, and the lifetime of species i, $\tau_i$. Equations 5 and 6 define $H_i(t)$ for species A and B respectively.

$$H_A(t) = \phi_A \exp(-t/\tau_A) \quad (5)$$

$$H_B(t) = \phi_B \exp(-t/\tau_B) \quad (6)$$

Third and subsequent species would add subsequent parameter pairs of $\tau_c$ and $\phi_c$. Any species that has a unique lifetime greater than 1 nanosecond will have a unique shape. Any species or compound with a lifetime less than 1 ns looks the same and any species greater than several microseconds becomes difficult to see. Fortunately, most species have excited state lifetime less than microseconds.

EXAMPLE 1

Figure 3:
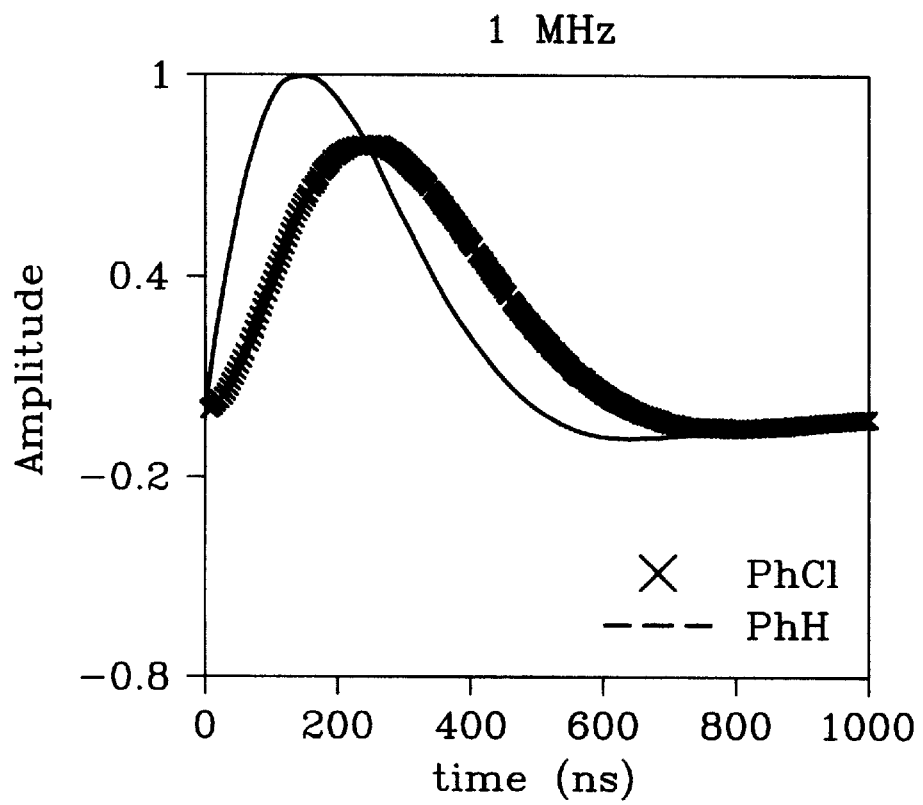
FIG. 3 is a graph of amplitude versus time for a model response of a 1 MHz transducer to a solution containing benzene and chlorobenzene.
Figure 4:
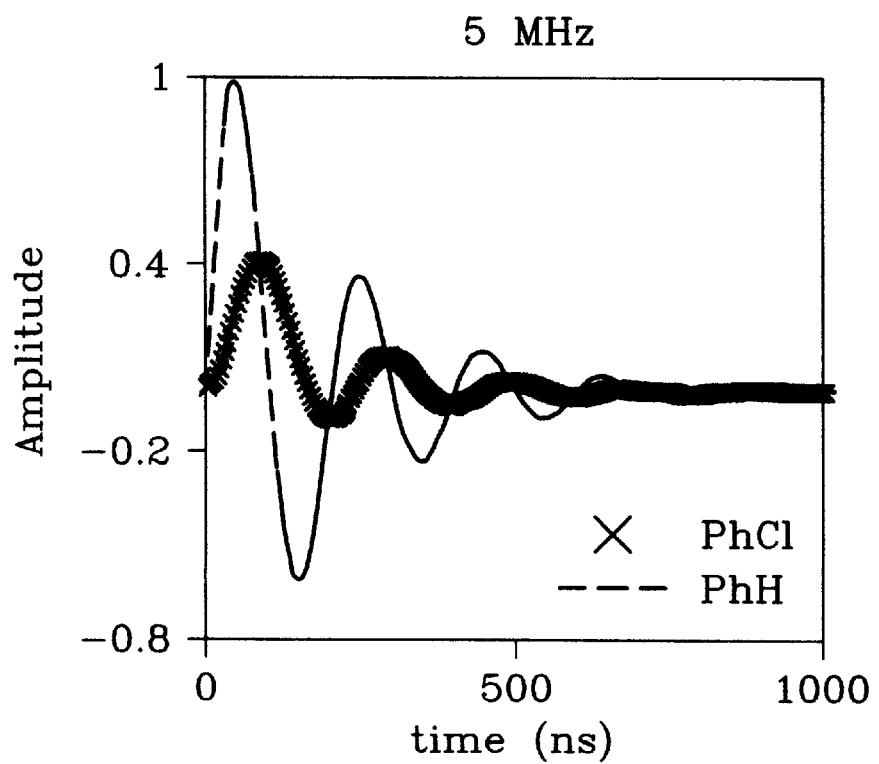
FIG. 4 is a graph of amplitude versus time for a model response of a 5 MHz transducer to the solution containing benzene and chlorobenzene.
Figure 5:
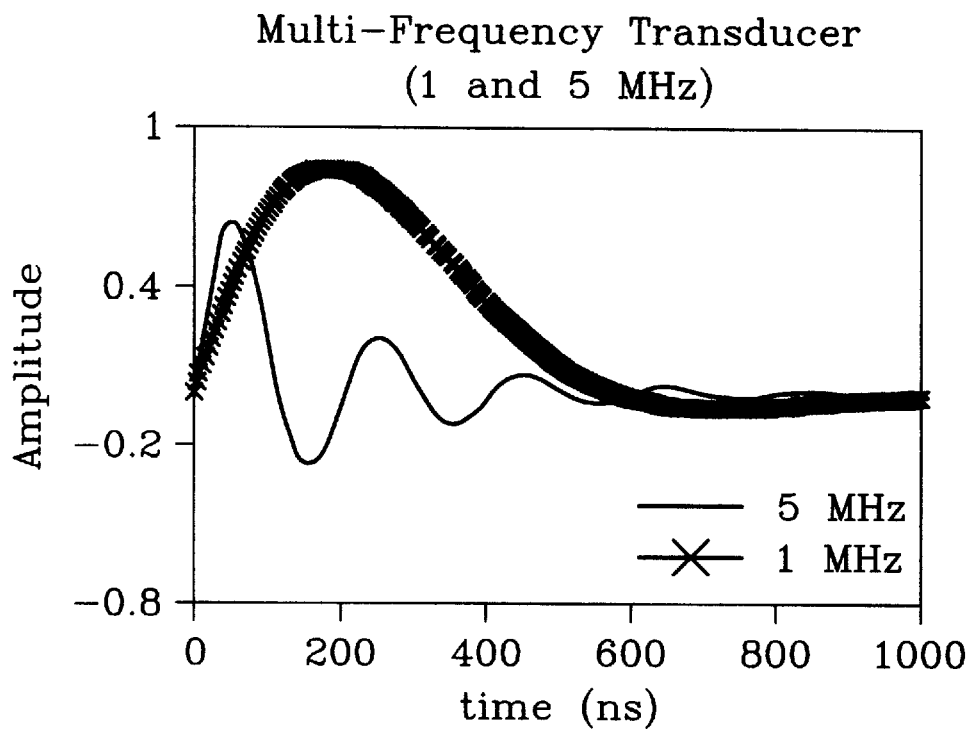
FIG. 5 is a graph of amplitude versus time for a model response of a dual frequency transducer (1 MHz and 5 MHz) to the solution containing benzene and chlorobenzene.

The time dependent response of a 1MHz, a 5MHz and a multi-frequency transducer are shown in FIGS. 3, 4 and 5. Species such as chlorobenzene that have a long-lived excited state lifetime provide a unique response (observed shape and amplitude) for a piezoelectric detector. Fourier analysis of the photoacoustic waveforms will yield the contributing frequencies that provide a unique shape and amplitude at each frequency. Different frequency transducers have an individual unique response to the time-dependent release of heat from an excited state molecule. Importantly there is only one unique solution for the parameters $\phi_A$, $\phi_B$, $\tau_A$ and $\tau_B$ that can be used to describe the shape and amplitude of the response provided by the dual frequency transducer for two absorbing species. An iterative analysis of the photoacoustic signals from more than one frequency will provide a unique solution to fit the shape and amplitude of the observed photoacoustic signals at each frequency observed thereby permitting operation without a standard.

FIG. 3 shows the response provided by a 1 MHz transducer to an absorbing species that has excited state lifetime of <1 ns and 100 ns respectively (for example benzene and chlorobenzene). FIG. 4 shows the response provided by a 5 MHz transducer to the same species. FIG. 5 shows the response of a dual frequency transducer to a mixture of a species with a short lifetime and one with a lifetime of 100 ns (e.g., chlorobenzene).

In a preferred embodiment, the transducer of the present invention is designed as an acoustic wave receiver transducer and neither the thickness of a wear plate nor the size nor the shape of the piezoelectric element is critical. In addition, a damping plate is optional. By omitting a damping plate, the spectral components near resonance may be enhanced with the added benefit of a receive mode transducer that may be reduced in size compared to a send/receive transducer by at least the length of the backing material. Thus the multi-frequency acoustic detector may be miniaturized in both length (minimum backing) and width (no restrictions on thickness to width ratio).

EXAMPLE 2

Figure 1B:
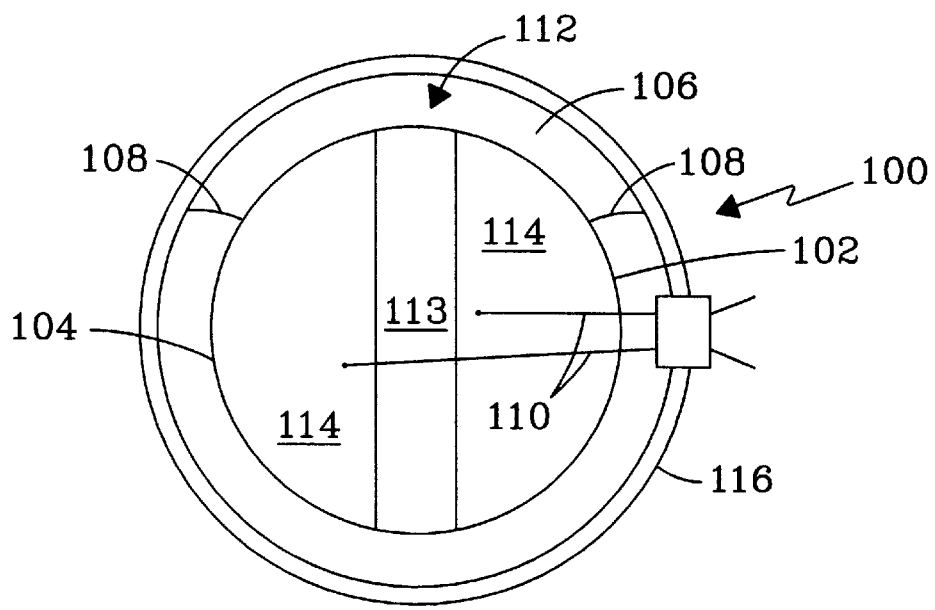
Figure 1C:
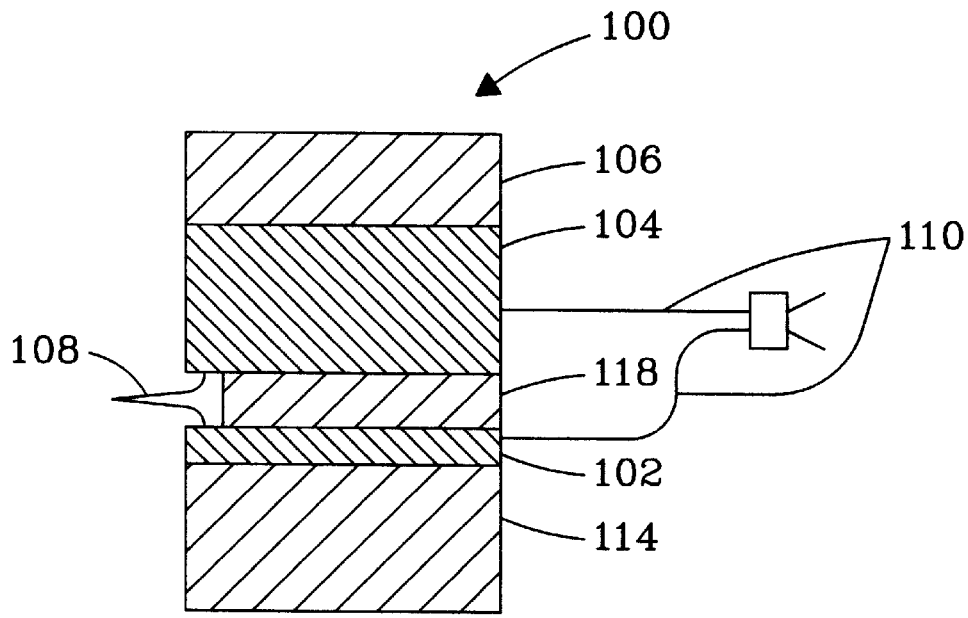
FIG. 1c is a cross section of a stacked element transducer.

A transducer 100 having a first piezoelectric element 102 of a first frequency of 5 MHz and a second piezoelectric element 104 of a second frequency of 1 MHz was fabricated as shown in FIGS. 1a, 1b. The piezoelectric elements, type Nova 3B, were obtained from KERAMOS, Indianapolis, Ind. The piezoelectric disks coated with silver electrodes were cut into hemi-circular shapes. The wear plate 106 was a spacer of ¼" thick quartz. Leads were attached to the electrodes and the cut crystals were affixed to the wear plate with degassed slow set epoxy as an assembly. The assembly was tightly clamped until the epoxy was set. A backing material 114 of an acoustic dampener was affixed with epoxy and clamped until the epoxy was set as a final assembly. The final assembly was placed into a housing.

Figure 6:
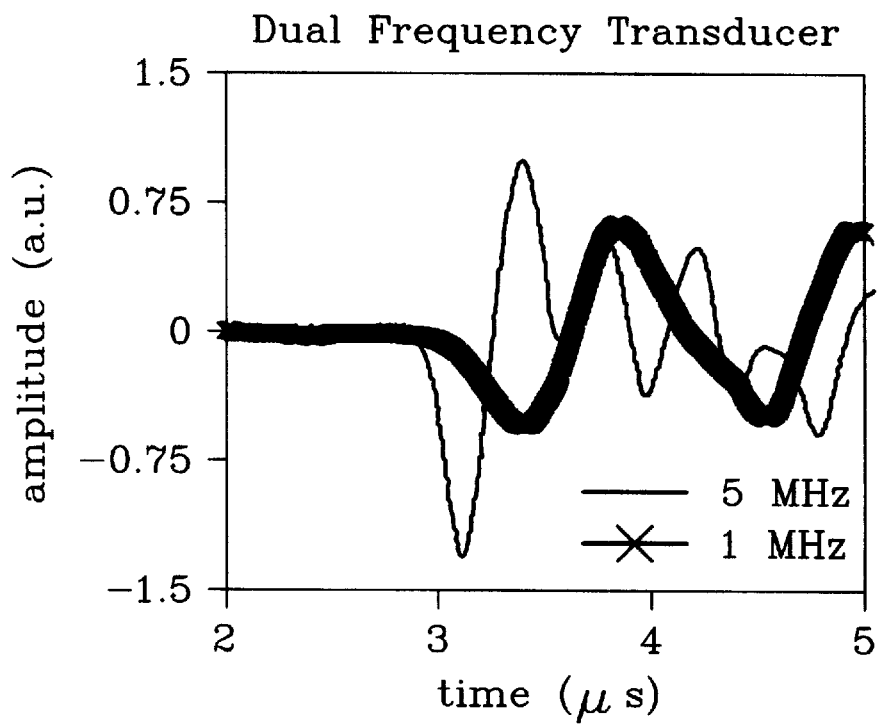
FIG. 6 is a graph of the photoacoustic waveform obtain from a dual frequency transducer (1 MHz/5 MHz) for a species with an excited state lifetime <1 nanosecond.

Results are shown in FIG. 6 of the photoacoustic waveform obtained with the dual frequency transducer 100. A species with an excited state lifetime <1 ns shows the response for both 1 MHz and 5 MHz piezoelectric elements obtained simultaneously. The side by side "parallel" construction of the piezoelectric elements within the transducer assured no interference from "cross-talk" between the different frequencies.

EXAMPLE 3

A stacked type dual frequency transducer (FIG. 2) was constructed. The 1 MHz crystal picked up signal from the 5 MHz crystal and the 5 MHz crystal picked up signal from the 1 MHz crystal leading to a mixed signal (cross-talk).

Closure

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. In a mixture containing at least two chemical species, a method for identifying and measuring concentration of said at least two chemical species, comprising the steps of:

passing electromagnetic energy through said mixture thereby creating a photoacoustic signal;

receiving said photoacoustic signal with at least two piezoelectric elements, wherein at least a first piezoelectric element has a first frequency, at least a second piezoelectric element has a second frequency, said at least two piezoelectric elements are longitudinal elements for longitudinal waves, and said first frequency is different from said second frequency; and fitting four parameters with said first and second frequencies.

2. The method as recited in claim 1, wherein said at least two piezoelectric elements are on a wear plate.

3. The method as recited in claim 2, wherein said at least two piezoelectric elements are placed independently on said wear plate.

4. The method as recited in claim 2, wherein said at least two piezoelectric elements are stacked on said wear plate.

5. The method as recited in claim 1, wherein said at least two piezoelectric elements are on separate wear plates.

6. The method as recited in claim 1, wherein said electromagnetic energy is pulsed excitation energy from a laser.

* * * * *